United States Patent [19]

Goldhorn et al.

[11] Patent Number: 5,416,824
[45] Date of Patent: May 16, 1995

[54] X-RAY DIAGNOSTICS APPARATUS

[75] Inventors: Klaus Goldhorn, Erlangen; Gerd Huettenrauch, Uttenreuth, both of Germany

[73] Assignee: Siemens Aktiengesellschaft, Munich, Germany

[21] Appl. No.: 213,083

[22] Filed: Mar. 15, 1994

[30] Foreign Application Priority Data

May 13, 1993 [DE] Germany .............. 43 16 130.8

[51] Int. Cl.⁶ .............................. G03B 42/02
[52] U.S. Cl. .................. 378/189; 378/195; 378/208
[58] Field of Search .......... 378/189, 208, 209, 210, 378/195, 198

[56] References Cited

U.S. PATENT DOCUMENTS

| | | | |
|---|---|---|---|
| 4,879,737 | 11/1989 | Grady | 378/195 |
| 5,014,292 | 5/1991 | Siczek et al. | 378/208 |

FOREIGN PATENT DOCUMENTS 7102644  1/1991  Germany .

OTHER PUBLICATIONS

Brochure for Siemens Siregraph D3 (No translation).

Primary Examiner—David P. Porta
Assistant Examiner—Don Wong
Attorney, Agent, or Firm—Hill, Steadman & Simpson

[57] ABSTRACT

An x-ray diagnostics apparatus has a height-adjustable patient support plate vertically mounted on a pedestal, and an x-ray image intensifier adjustably mounted beneath the support plate at the pedestal. The x-ray image intensifier is mounted so as to be adjustable in position between an exposure position and a standby position. In the standby position, the image intensifier does not interfere with lowering of the support plate, which can thus be lowered to a position to more easily accommodate placement of a patient on the support plate. The x-ray image intensifier can be horizontally aligned in the standby position, or can be located outside the region of the support plate.

9 Claims, 3 Drawing Sheets

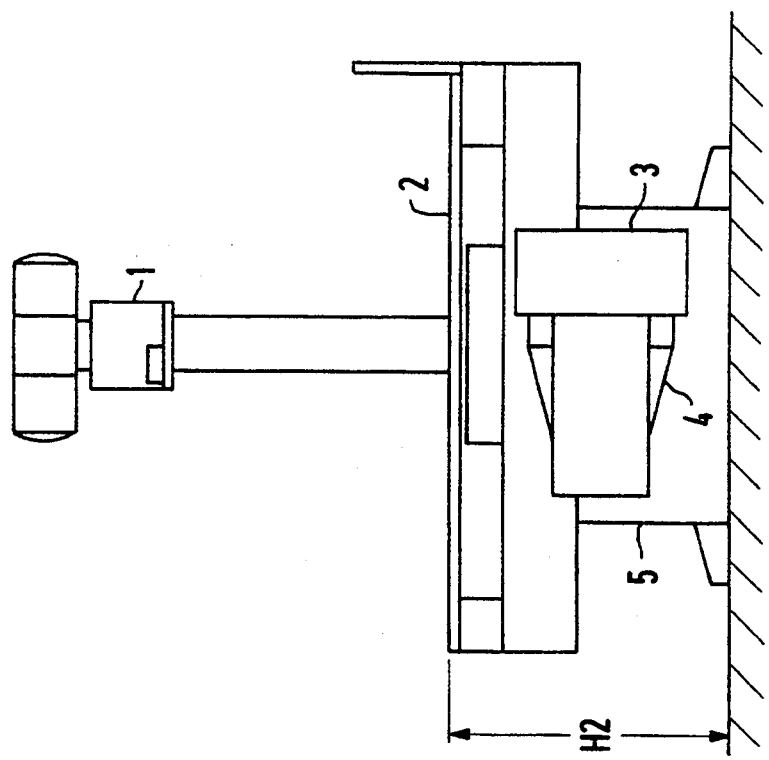
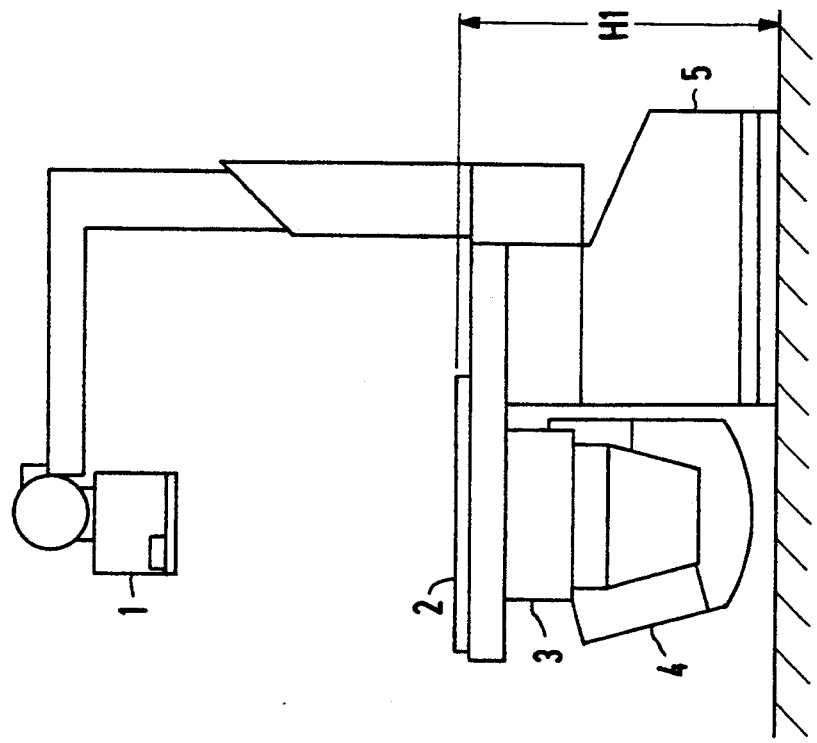

X-RAY DIAGNOSTICS APPARATUS

BACKGROUND OF THE INVENTION

1. Field of the Invention

The present invention is directed to an x-ray diagnostics apparatus of the type having a patient support plate which is height-adjustably mounted at a pedestal, and an x-ray image intensifier which is adjustably disposed at the pedestal.

2. Description of the Prior Art

A commercially available x-ray diagnostics apparatus of the type described above, known as the SIRE-GRAPH D3, is sold by Siemens. In this so-called above-table apparatus, the lowest possible height of the support plate, as measured from the floor, is essentially dependent on the structural length (vertical height) of the image intensifier which is located beneath the support plate. In systems having a large image intensifier having a large structural length, the lowest possible height of the support plate above the floor is consequently also large, making patient transfer onto the support plate more difficult. Transferring a bed-ridden patient from a gurney to the support plate is extremely personnel-intensive when there is a relatively large height difference between the gurney and the support plate. More gurneys are not height-adjustable, but if too great a difference in height exists, such a height-adjustable gurney must be used, which is considerably more expensive than a conventional gurney. In the case of patients who can position themselves on the support plate unassisted, climbing aids are nonetheless still provided such as a portable set of steps. The use of such climbing aids, however, can result in accidents causing injury to the patient, and if the climbing aid is neglected to be removed after the patient is on the support plate, collisions between the climbing aid and components of the examination apparatus can occur during the examination. Such collisions not only lead to interruptions in the examination, but may possibly cause damage requiring servicing of the installation.

SUMMARY OF THE INVENTION

It is an object of the present invention to provide an x-ray diagnostics apparatus of the type having a support plate which is height-adjustable at a pedestal, and which has an x-ray image intensifier disposed, for examination purposes beneath the support plate, which makes patient transfer onto the support plate less personnel-intensive, and which permits such transfer to take place without the use of a height-adjustable gurney and without the use of climbing aids.

The above object is achieved in accordance with the principles of the present invention in such an installation having means for adjusting the position of the x-ray image intensifier from an exposure position into a standby position, the x-ray image intensifier in the standby position not impeding lowering of the support plate. This permits the support plate to be lowered to a convenient and comfortable height for either transferring a patient from a standard gurney, or to permit the patient to climb unassisted onto the support plate without the need of a step stool.

The x-ray image intensifier in the inventive installation occupies less space in the standby position than in the exposure position, so that the support plate can be adjusted to a lower height above the floor than would otherwise be possible. Preferably, the x-ray image intensifier is mounted so as to be pivotable from a vertical exposure position into a horizontal standby position. Because x-ray image intensifiers have a smaller structural width than structural length, the support plate can be lowered to a greater extent if it is limited only by the structural width of the x-ray image intensifier, instead of the structural length thereof. In conventional x-ray diagnostics systems, the x-ray image intensifier is mounted and oriented so that it is the structural length which is the limiting factor in the extent to which the support plate can be lowered.

In an alternative embodiment, the standby position of the x-ray image intensifier is outside of the region of the support plate, thereby permitting the support plate to be lowered even farther.

Preferably the x-ray image intensifier is pivotable around an axis by means of a mount for this purpose.

Preferably mechanical control means are provided which, proceeding from the exposure position in a first range of adjustment, effect adjustment of the x-ray image intensifier in the vertical direction and, in a further range of adjustment, effect pivoting of the x-ray image intensifier around the aforementioned axis before the standby position is reached.

DESCRIPTION OF THE DRAWINGS

FIG. 1 shows an end elevational view of an x-ray diagnostics apparatus constructed in accordance with the principles of the present invention, with the x-ray image intensifier in the exposure position.

FIG. 2 shows a side elevational view of the x-ray diagnostics apparatus of Figure 1, but with the x-ray image intensifier in the standby position.

DESCRIPTION OF THE PREFERRED EMBODIMENTS

Figure 3:
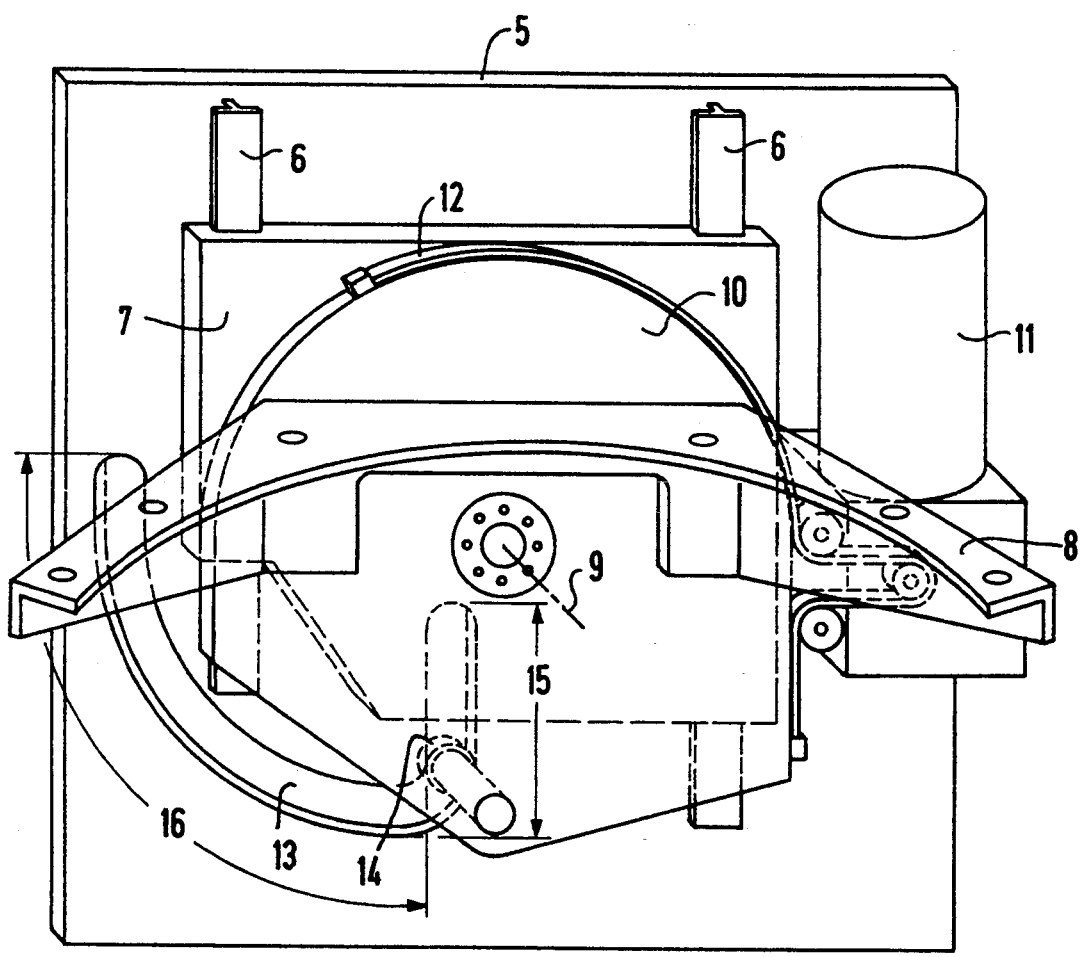
FIG. 3 shows a mounting mechanism for an x-ray image intensifier for use in the x-ray diagnostics apparatus of FIG. 1 and 2.

The exemplary x-ray diagnostics apparatus shown in FIGS. 1 and 2 has an x-ray radiator 1 which is located above the further components of the apparatus, namely a unit composed of a support plate 2, an x-ray image intensifier 3, and a mount 4 for the x-ray image intensifier 3. The support plate 2 is mounted so as to be height-adjustable on a pedestal 5, at which the mount 4 is also seated. The x-ray image intensifier 3 is adjustable by means of the mount 4 and, as shown in FIG. 1, is located in an exposure position. Since a collision of the x-ray image intensifier 4 with the floor is to be avoided, the smallest permissible height $H_1$ between the floor and the support plate 2 is relatively large, as is the case as well with conventional x-ray diagnostics systems known in the art.

Proceeding from FIG. 1, wherein the x-ray image intensifier 3 is in a vertical position, the x-ray image intensifier 3 can be pivoted in accordance with the principles of the present invention into a standby position as shown in FIG. 2. In the standby position the x-ray image intensifier 3 is, for example, horizontally disposed. Because x-ray image intensifiers such as the x-ray image intensifier 3 generally have a larger structural length than structural width, the support plate 2 in the x-ray diagnostics apparatus of the invention can assume a smaller height $H_2$ above the floor in comparison to conventional systems. The smaller height $H_2$ of the support plate 2 permits a patient to be examined to climb onto the support plate 2, if able to do so unassisted, without a climbing aid being required. Moreover, bedridden patients can be transferred onto the support plate form a gurney without having to be lifted by attending personnel, and without the necessity of using a height-adjustable gurney.

FIG. 3 shows an exemplary embodiment of a mount 4 for the x-ray image intensifier 3 for use in the apparatus shown in FIGS. 1 and 2, by means of which the x-ray image intensifier 3 can be adjusted from the exposure position to the standby position. For this purpose, the mount 4 includes a carriage 7 which is mounted to the pedestal 5 by means of rails 6. The carriage 7 carries a bracket 8 for the x-ray image intensifier 3. The bracket 8 is rotatable around a horizontal axis 9 by virtue of attachment to a rotary table 10 having a central bearing permitting rotation around the horizontal axis 9. An electromechanical drive 11 operates at least one driven geared wheel which engages a toothed belt 12 extending around a portion of the periphery of the rotary table 10. The toothed belt 12 has opposite ends which are attached to the rotary table 10, but is otherwise not attached to the periphery. A cam slot 13 has a peg 14 movable therein, the peg 14 being mounted on the rotary table 10. When the rotary table 10 is caused to rotate around the horizontal axis 9 by operation of the electromechanical drive 11, the bracket 8 is adjusted in the vertical direction starting from an upper exposure position in a first region 15 of the cam slot 13, because the toothed belt 12 is being moved along the vertical portion of the periphery of the rotary table 10. As the belt 12 begins to be lifted away from the curved portion of the rotary table 10, the peg 14 moves into a second adjustment region 16 of the cam slot 13, thereby causing the rotary table 10, and the bracket 8 to be rotated around the horizontal axis 9. The x-ray image intensifier 3 thus is adjusted into the horizontal standby position.

Figure 4:
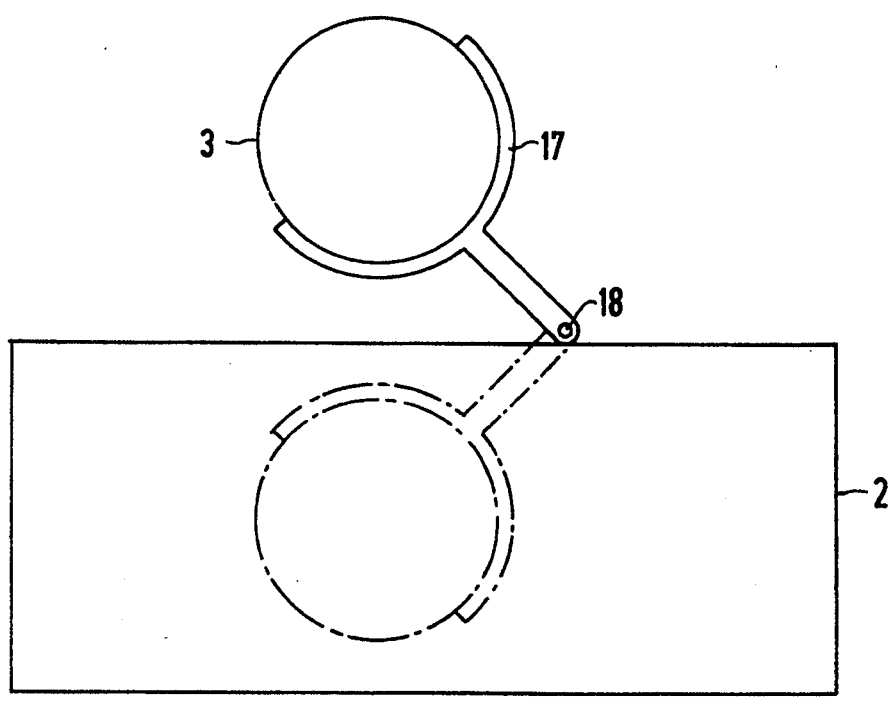
FIGS. 4 and 5 respectively schematically illustrate further embodiments of the x-ray diagnostics apparatus of the invention, in plan views.

A further exemplary embodiment of the invention is schematically shown in FIG. 4, wherein the image intensifier 3 is pivotable proceeding from an exposure position into a standby position around a vertical axis 18 via a second mount 17. In the exposure position, the x-ray image intensifier 3 is located beneath the support plate 2, and in the standby position the x-ray image intensifier 3 is located outside the region of the support plate 2, i.e., it is not all beneath the support plate 2.

Figure 5:
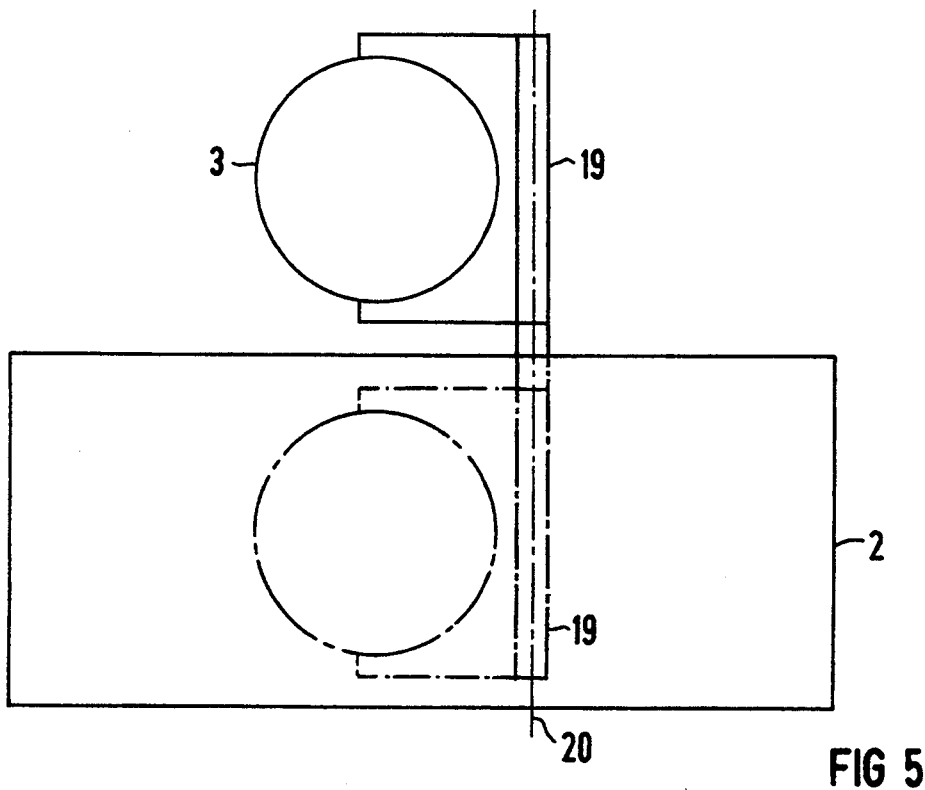

A further exemplary embodiment is shown FIG. 5, wherein the x-ray image intensifier 3 is adjustable along a horizontal axis 20 by means of a third mount 19. The x-ray image intensifier 3 can thus be adjusted from the exposure position beneath the support plate 2 into a standby position next to the support plate 2. This movement can endue along a horizontally disposed rail, or by means of a telescoping mechanism.

In the exemplary embodiments of the invention shown in FIGS. 4 and 5, the x-ray image intensifier 3 does not at all limit the minimum height of the support plate 2 above the floor, because it is situated outside the region of the support plate 2.

Although modifications and changes may be suggested by those skilled in the art, it is the intention of the inventors to embody within the patent warranted hereon all changes and modifications as reasonably and properly come within the scope of their contribution to the art.

We claim as our invention:

1. An x-ray diagnostics apparatus disposed on a floor, comprising:
   a pedestal;
   a height-adjustable patient support plate mounted on said pedestal for adjustment in height above said floor;
   an x-ray image intensifier having a longitudinal axis and having a structural height along said longitudinal axis; and
   means for mounting said x-ray image intensifier at said pedestal for adjusting said x-ray image intensifier between an exposure position situated beneath said patient support plate with said longitudinal axis vertically disposed and a standby position with said longitudinal axis horizontally disposed permitting lowering of said patient support plate relative to said floor unlimited by said structural height of said x-ray image intensifier.

2. An x-ray diagnostics apparatus as claimed in claim 1 wherein said means for mounting comprises means for moving said x-ray image intensifier from said exposure position to a standby position which is situated outside of the region of said patient support plate.

3. An x-ray diagnostics apparatus as claimed in claim 1 wherein said means for mounting includes a rotary table to which said x-ray image intensifier is attached, and means for rotating said rotary table around a central, horizontal axis to move said x-ray image intensifier between said exposure position and said standby position.

4. An x-ray diagnostics apparatus as claimed in claim 3 wherein said rotary table includes cam means for, in a first adjustment region, adjusting the position of said x-ray image intensifier in a vertical direction and, in a second adjustment region, pivoting said x-ray image intensifier around said horizontal axis before said standby position is reached.

5. An x-ray diagnostics apparatus as claimed in claim 4 wherein said rotary table has a periphery with a substantially vertical portion and a curved portion, and wherein said drive means includes a driven toothed wheel engaging a toothed belt having opposite ends attached to said periphery of said rotary table and engaging said periphery between said opposite ends, said drive means operating said toothed belt in said vertical region when said cam means is in said first adjustment region and operating said toothed belt in said curved region when said cam means is in said second adjustment region.

6. An x-ray diagnostics apparatus as claimed in claim 1 further comprising an x-ray source, and means for mounting said x-ray source to always remain higher above said floor than said x-ray image intensifier.

7. An x-ray diagnostics apparatus as claimed in claim 6 wherein said x-ray image intensifier has a longitudinal axis along which said structural height extends, and said means for mounting said x-ray image intensifier comprises means for pivoting said x-ray image intensifier from an exposure position in which said longitudinal axis is vertically disposed to a standby position in which said longitudinal axis is horizontally disposed.

8. An x-ray diagnostics apparatus disposed on a floor, comprising:
   a pedestal;
   a height-adjustable patient support plate mounted on said pedestal for adjustment in height above said floor;

an x-ray image intensifier having a structural height; and means for mounting said x-ray image intensifier at said pedestal for pivoting said x-ray image intensifier around a vertical axis between an exposure position situated beneath said patient support plate and a standby position situated outside of the region of said patient support plate for permitting lowering of said patient support plate relative to said floor unlimited by said structural height of said x-ray image intensifier.

9. An x-ray diagnostics apparatus as claimed in claim 8 further comprising an x-ray source, and means for mounting said x-ray source to always remain higher above said floor than said x-ray image intensifier.

* * * * *